(12) United States Patent
Thery

(10) Patent No.: US 8,765,472 B2
(45) Date of Patent: Jul. 1, 2014

(54) METHODS AND DEVICE TO CONSTRAIN MULTICELLULAR ARRANGEMENTS IN STABLE, STATIONARY AND REPRODUCIBLE SPATIAL CONFIGURATION

(75) Inventor: Manuel Thery, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 75 days.

(21) Appl. No.: 13/121,986

(22) PCT Filed: Oct. 23, 2009

(86) PCT No.: PCT/EP2009/063947
§ 371 (c)(1),
(2), (4) Date: May 18, 2011

(87) PCT Pub. No.: WO2010/046459
PCT Pub. Date: Apr. 29, 2010

(65) Prior Publication Data
US 2011/0223591 A1 Sep. 15, 2011

Related U.S. Application Data

(60) Provisional application No. 61/193,031, filed on Oct. 23, 2008.

(30) Foreign Application Priority Data

Oct. 24, 2008 (EP) .................................... 08305722

(51) Int. Cl.
*C12N 5/00* (2006.01)
*C12N 11/18* (2006.01)
(52) U.S. Cl.
USPC .......................................... 435/395; 435/175
(58) Field of Classification Search
USPC .................................................. 435/395, 175
See application file for complete search history.

(56) References Cited

U.S. PATENT DOCUMENTS

| 5,470,739 A | 11/1995 | Akaike et al. |
| 5,976,826 A * | 11/1999 | Singhvi et al. ................. 435/29 |
| 2008/0032403 A1 | 2/2008 | Saito et al. |

FOREIGN PATENT DOCUMENTS

WO   WO 2005/026313   3/2005

OTHER PUBLICATIONS

Huang et al. Symmetry-Breaking in Mammalian Cell Cohort Migration During Tissue Pattern Formation: Role of Random-Walk Persistence. Cell motility and the Cytoskeleton (2005) 61:201-213.*
Nelson, C. M. et al. "VE-cadherin simultaneously stimulates and inhibits cell proliferation by altering cytoskeletal structure and tension" *Journal of Cell Science*, Sep. 1, 2003, pp. 3571-3581, vol. 116, No. 17.
Huang, S. et al. "Symmetry-Breaking in Mammalian Cell Cohort Migration During Tissue Pattern Formation: Role of Random-Walk Persistance" *Cell Motility and the Cytoskeleton*, Aug. 2005, pp. 201-213, vol. 61, No. 4.
Fink, J. et al. "Comparative study and improvement of current cell micro-patterning techniques" *Lab on a Chip*, Jun. 2007, pp. 672-680, vol. 7, No. 6.
Written Opinion in International Application No. PCT/EP2009/063947, Oct. 23, 2009, pp. 1-9.

* cited by examiner

*Primary Examiner* — Karen Cochrane Carlson
*Assistant Examiner* — Natalie Moss
(74) *Attorney, Agent, or Firm* — Saliwanchik, Lloyd & Eisenschenk

(57) ABSTRACT

The present invention relates to methods and devices to obtain multicellular arrangements in stable, stationary and reproducible spatial configuration, and optionally with controlled internal cell organization, methods for preparing such devices, methods for studying the cells' shapes, the cells' architectures, the cells' mechanical equilibrium, the cell-cell interaction, the cell movement and migration, the cell differentiation, the global internal cells' organizations, the cells' polarities and division, and/or any function of cells, methods for screening compounds of interest which enhance or inhibit specific cell functions.

17 Claims, 9 Drawing Sheets

Figure 1:
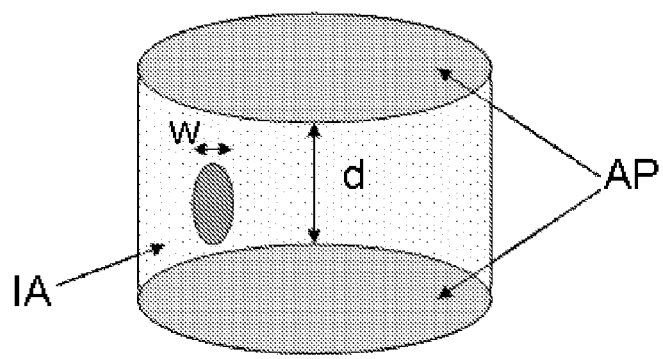

METHODS AND DEVICE TO CONSTRAIN MULTICELLULAR ARRANGEMENTS IN STABLE, STATIONARY AND REPRODUCIBLE SPATIAL CONFIGURATION

CROSS-REFERENCE TO RELATED APPLICATIONS

This application is the U.S. national stage application of International Patent Application No. PCT/EP2009/063947, filed Oct. 23, 2009, which claims the benefit of U.S. Provisional Patent Application No. 61/193,031, filed Oct. 23, 2008, the disclosures of which are hereby incorporated by reference in their entireties, including all figures, tables and amino acid or nucleic acid sequences.

FIELD OF THE INVENTION

The present invention relates to the field of cellular biology and can be useful in biochips, screening of compounds of interest, diagnostics and cellular/gene therapy. In particular, the present invention relates to methods and devices to obtain multicellular arrangements in stable, stationary and reproducible spatial configuration.

BACKGROUND OF THE INVENTION

The cells in culture adopt a random spatial organization in which the positioning of the cells is unforeseeable. The cells are permanently pulled and pushed. They thus move according to the fluctuations of the intercellular interactions. No tool making it possible to control the positions and the shapes of the cells within these multicellular arrangements is available.

There are some tools to isolate cells from each others and control their shapes: the micro-patterning. Accordingly, adhesive patterns can be prepared by grafting extracellular matrix proteins on a solid support. Those proteins induce cellular adherence and promote cell attachment and flattening on the solid support. Consequently, cells can be confined in squares, rounds, triangles or more complex geometries, their size corresponding to the size of a cell. Cells have then all the same shape and even can adopt very reproducible internal organizations. Suitable micro-patterns have been disclosed in the PCT application WO 2005/026313. However, cells thus constrained are isolated and are not in direct contact with other cells. Accordingly, each cell is isolated from the other cells on an adhesive pattern by surrounding cytophobic regions in order to avoid any contact between cells immobilized on the support. The size of the adhesive pattern is such as one single cell could spread. This is the major drawback of this technology.

Indeed, the biologic mechanisms controlling the mechanic and functional coherence of a tissue by regulating the size, shape and position of cells do not only depend on the cell anchorage with extracellular matrix but also on the attachments of cells to the neighbouring cells. The cell-cell interactions, in addition to their mechanical role, also contribute to biochemical signalization pathways that regulate cellular activities as important as the proliferation, the differentiation and the apoptosis. In order to reproduce in a cell culture the conditions of a cell in a tissue, two types of contact are therefore needed: contacts with the extracellular matrix and contacts between cells.

The simplest solution to reach the shape control of a group of several cells from the one of an individual cell is to use a larger micro-pattern (Nelson and Chen, 2002, *FEBS Letters*, 514, 238-242).

However, the micro-patterning technology reaches its limit in this context. Indeed, when two cells are constrained on a same pattern, they can establish the two types of contact (cell-matrix with the adhesive pattern and cell-cell with the neighbouring cells), but they can also move and for instance take the place of the other cell. Hence, they tend to move around each other. They do not adopt a mechanical equilibrium allowing them to stabilize in one stationary configuration. Scientific articles were devoted to the movement of a pair of cells on micro-patterns (Brangwynne et al, 2000, In Vitro Cell Dev Biol Anim, 36, 563-5; Huang et al, 2005, Cell Motil Cytoskeleton, 61, 201-213). In addition, the cells position, the position and size of cell-cell contact zone are not controlled so as the polarity and the internal organization (Nelson and Chen, 2002). In Huang et al, 2005, the authors observed that two NIH 3T3 cells on a square pattern did not move around each other and formed a straight cell-cell boundary stretching diagonally between opposite corners of the square.

Nelson et al develops another system to control the position of cells and the cell-cell contact (Nelson and Chen, 2002, supra; Nelson and Chen, 2003, J Cell Science, 116, 3571-3581). Cells are constrained in agarose micro-wells of about 10 µm of depth. Micro-wells have a bow-tie shape. Agarose prevents protein adsorption and cell adhesion. When two cells are present in a micro-well, each cell is located in one of the two triangular forms of the bow-tie shape. The micro-wells depth and their agarose composition allow the constraint of the cells into the triangular forms and the cells cannot step over to move into the other triangular half. However, in such bow-tie shaped micro-wells, the structure of actin does not seem to be well controlled. In addition, the intercellular contact zone is narrowed to the bottle neck between the two triangular forms and the bottle neck has to be narrow for preventing cells to move into the other triangular half. In addition, the cells are not in a mechanical equilibrium. Indeed, the cell position is restrained by the form of the bow-tie shaped micro-wells. Accordingly, the cell configuration is not based on mechanical interaction between cells. Therefore, the conformation is artefactitious and does not reproduce the physiological conditions of cells in a tissue.

Accordingly, there is a strong need of methods and devices to obtain multicellular arrangements in stable, stationary and reproducible spatial configuration, and optionally with controlled internal cell organization.

SUMMARY OF THE INVENTION

The present invention provides methods and devices to obtain a mechanical equilibrium within multicellular arrangements. In particular, it provides adhesive patterns with specific geometries preventing the rotating movement of cells and conferring them spatial adhesive conditions allowing achievement of a mechanical equilibrium and a stationary and reproducible conformation. Indeed, the pattern geometry allows the control of cell-matrix anchorage points in order to prevent the movements of these anchorage points and then the cell migration on the pattern. In addition, the pattern geometry orientates the cell-cell contact in stable and reproducible way. In particular, large cell-cell contact can be obtained with the methods and devices of the invention. The spatial distribution of the anchorage points between matrix and cell and between cells leads to a mechanical equilibrium and cells don't move. In addition, methods and devices of the present invention also allow obtaining reproducible internal cell organisation.

Accordingly, the present invention concerns methods and devices for adhering at least two cells in a multicellular arrangement with a mechanically stable and reproducible conformation.

The present invention concerns the use of a device for adhering at least two interacting cells in a multicellular arrangement with a mechanically stable and reproducible conformation, comprising:
 a plate defining a plane surface; and,
 a set of at least two adhesive patterns, wherein the at least two adhesive patterns are sufficiently separated from each other by an essentially non-adhesive intercalating area for preventing a cell on a first adhesive pattern to reach another adhesive pattern; and, the area covered by the at least two adhesive patterns and the intercalating area is sufficient to adhere at least two animal cells, and wherein the set of at least two adhesive patterns is isolated by a cytophobic surrounding region.

In particular, the present invention also concerns a device for or suitable for adhering at least two interacting cells in a multicellular arrangement with a mechanically stable and reproducible conformation, comprising:
 a plate defining a plane surface; and,
 a set of at least two adhesive patterns, wherein the at least two adhesive patterns are sufficiently separated from each other by an essentially non-adhesive intercalating area for preventing a cell on a first adhesive pattern to reach another adhesive pattern; and, the area covered by the at least two adhesive patterns and the intercalating area is sufficient to adhere at least two animal cells, and wherein the set of at least two adhesive patterns is isolated by a cytophobic surrounding region.

Preferably, the distance between two adhesive patterns is comprised between about $2/3$ D and about $4/3$ D, D being the diameter of a disk having said surface S, preferably between about $3/4$ D to about $5/4$ D, more preferably about D.

Preferably, the area covered by the adhesive pattern for each cell is less than 80, 70, 60 or 50% of the cell surface S. Preferably, the essentially non-adhesive intercalating area comprises a single adhesive zone suitable for not allowing a cell to reach another adhesive pattern. More preferably, the single adhesive zone is a zone located between two adhesive patterns and having a width of less than $1/2$ D, preferably less than $1/3$ D, more preferably less than $1/4$ D. Preferably, the single adhesive zone connects the two adhesive patterns, thereby the set of two adhesive patterns comprises a single adhesive zone connecting the two adhesive patterns. In a preferred embodiment, the set of two adhesive patterns has one of the following forms: C, X, H, Z and Π. In particular, the adhesive patterns can be formed of single connected adhesive surfaces and/or of several non-connected adhesive surfaces. Preferably, the device comprises at least 2 sets of at least two adhesive patterns. Alternatively, the device comprises at least 2 sets of at least 4, 8, 16 or 32 adhesive patterns. In particular, each set of adhesive patterns can be designed for a multicellular arrangement with more than two cells and covers an area of more than 2500 $\mu m^2$, preferably between 2600 and 50000 $\mu m^2$, for instance 2600, 3000, 3500, 4000, 4500, 5000, 6000, 7000, 8000, 9000, 10000, 20000, 30000, 40000 or 50000 $\mu m^2$. Indeed, a set of adhesive patterns for 32 cells can cover a surface of 32000 $\mu m^2$ and, even 50000 $\mu m^2$ for particular cell types.

The present invention also concerns the use of a device of the present invention for screening a compound of interest, for identifying a gene of interest, or for the diagnostic of a cell dysfunction.

The present invention concerns a method for adhering at least two interacting cells in a multicellular arrangement with a mechanically stable and reproducible conformation, comprising:
 selecting the cells to be adhered;
 selecting an appropriate device according to the present invention; and,
 culturing the cells on the selected device.

Preferably, the method comprises determining the surface covered by the cells on a support without any constraint in order to determine the size of the cells and selecting the device based on the size of the cells.

The present invention further concerns a method for immobilizing at least two cells at a plane surface in a multicellular arrangement with a mechanical equilibrium, said method comprising:
 providing a device of the present invention; and,
 exposing the plate to at least one cell for a period of time sufficient to allow the cell(s) to divide into at least two cells on said set of adhesive patterns and to adhere to each said adhesive pattern and reach a multicellular arrangement with a mechanical equilibrium.

Alternatively, the present invention concerns a method for immobilizing at least two cells at a plane surface in a multicellular arrangement with a mechanical equilibrium, said method comprising:
 providing a device of the present invention; and,
 exposing the plate to at least two cells for a period of time sufficient to allow the cell(s) to adhere to each said adhesive pattern and to reach a multicellular arrangement with a mechanical equilibrium.

In addition, the present invention concerns a method studying the cell shape, the cell movement and migration, the cell-cell interaction, the cell architecture, the cell differentiation, the cell polarity, the global internal cell organization, the cell division and/or any function of cells in a multicellular arrangement, said method comprising:
 providing a device of the present invention;
 exposing the plate to at least one cell for a period of time sufficient to allow the cell(s) to divide into at least two cells on said set of adhesive patterns and to adhere to each said adhesive pattern and reach a multicellular arrangement with a mechanical equilibrium; or exposing the plate to at least two cells for a period of time sufficient to allow the cell(s) to adhere to each said adhesive pattern and to reach a multicellular arrangement with a mechanical equilibrium;
 growing the cells on the set of adhesive patterns in the multicellular arrangement; and,
 observing and measuring the cell shape, the cell movement and migration, the cell-cell interaction, the cell architecture, the cell differentiation, the cell polarity, the global internal cell organization, the cell division and/or any function of cells in the multicellular arrangement.

The invention also concerns a method of selecting biologically active compounds, said method comprising:
 providing a device according to the present invention;
 exposing the plate to at least one cell for a period of time sufficient to allow the cell(s) to divide into at least two cells on said set of adhesive patterns and to adhere to each said adhesive pattern and reach a multicellular arrangement with a mechanical equilibrium; or exposing the plate to at least two cells for a period of time sufficient to allow the cell(s) to adhere to each said adhesive pattern and to reach a multicellular arrangement with a mechanical equilibrium;

contacting a test compound with said cells in the multicellular arrangement;

growing the cells on the adhesive patterns in the multicellular arrangement; and, observing the shape, the cell movement and migration, the cell-cell interaction, the cell architecture, the global internal cell organization, the cell differentiation, the cell polarity, the cell division and/or any function of said cells in the multicellular arrangement.

Alternatively, the invention further concerns a method of selecting biologically active compounds, said method comprising:

providing a device according to the present invention;

contacting a test compound with cells;

exposing the plate to at least one of said cells for a period of time sufficient to allow the cell(s) to divide into at least two cells on said set of adhesive patterns and to adhere to each said adhesive pattern and reach a multicellular arrangement with a mechanical equilibrium; or exposing the plate to at least two of said cells for a period of time sufficient to allow the cell(s) to adhere to each said adhesive pattern and to reach a multicellular arrangement with a mechanical equilibrium;

growing the cells on the adhesive patterns in the multicellular arrangement; and, observing the shape, the cell movement and migration, the cell-cell interaction, the cell architecture, the global internal cell organization, the cell differentiation, the cell polarity, the cell division and/or any function of said cells in the multicellular arrangement.

LEGEND TO THE FIGURES

FIG. 1: Schematic representation of a set of two adhesive patterns (AP) with the intercalating area (IA). The grey indicates adhesive areas. (d) defines the distance between the two adhesive patterns (AI). The intercalating area (IA) comprises an adhesive zone (in grey) and (w) defines the width of this adhesive zone. It has to be noticed that this representation is not limiting and its goal is to well define the terms. For instance, the adhesive zone of the intercalating area (AI) can be central or at the left or right end of the pattern and can connect or not one or both adhesive patterns.

Figure 2:
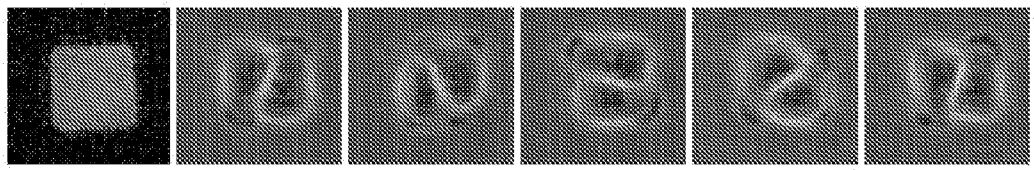

FIG. 2: Time-lapse phase contrast microscopy of MCF10A epithelial daughter cells after division on a square adhesive pattern. The cells keep moving around each other for hours until the next division.

Figure 3:
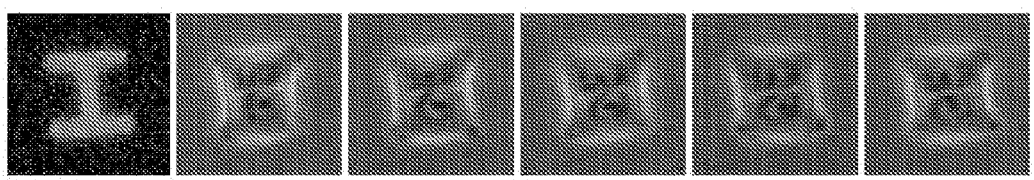

FIG. 3: Time-lapse phase contrast microscopy of MCF10A epithelial daughter cells after division on a H-shape adhesive pattern. Cells don't move around each other. They adopt a mechanical equilibrium and don't move until the next division.

Figure 4:
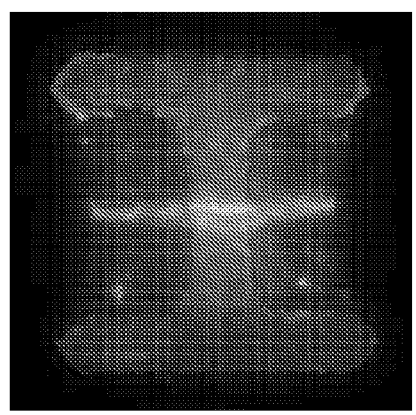

FIG. 4: Two MCF10A epithelial daughter cells in a mechanical equilibrium on H-shape fibronectin-adhesive pattern. Cell-cell contacts are always located in a plane bisecting the central bar of the H-shape. The nuclei are always close to the cell-cell interaction plane.

Figure 5:
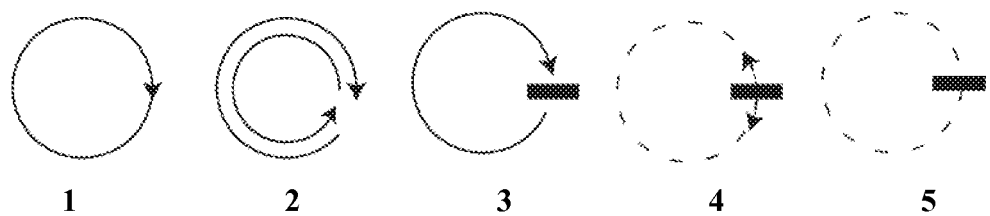
Figure 5:
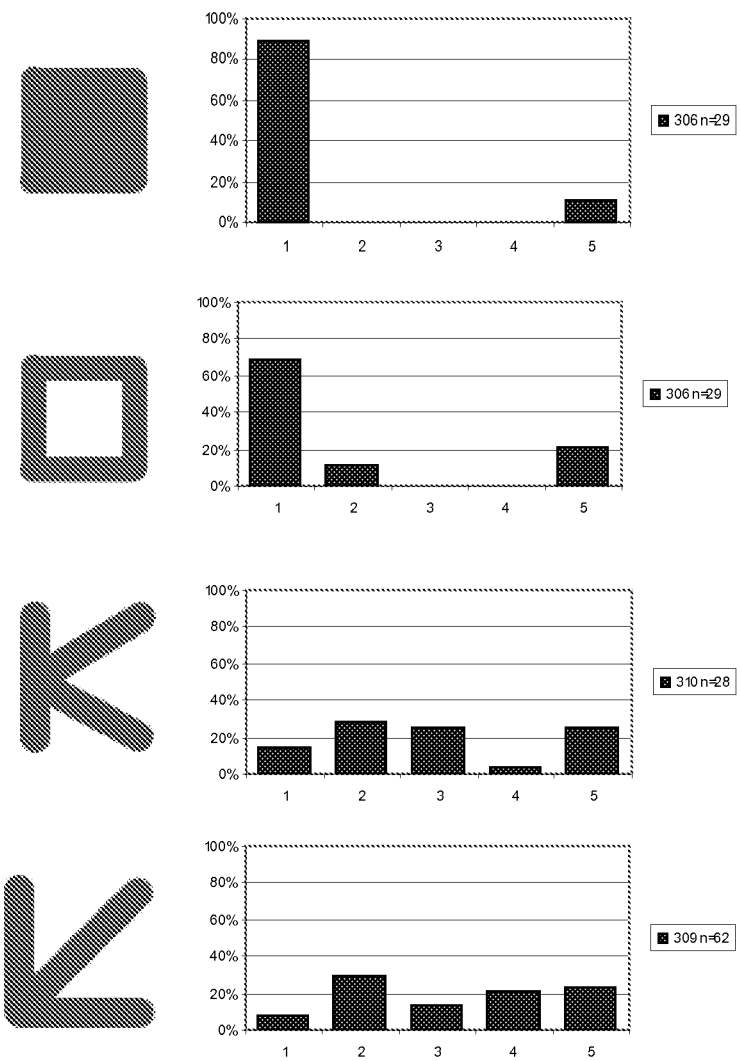
Figure 5:
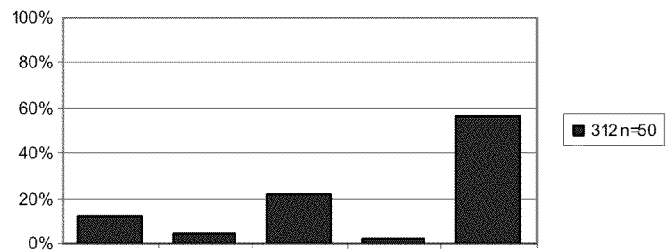
Figure 5:
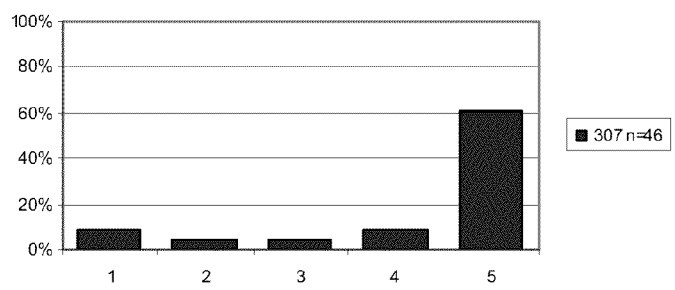
Figure 5:
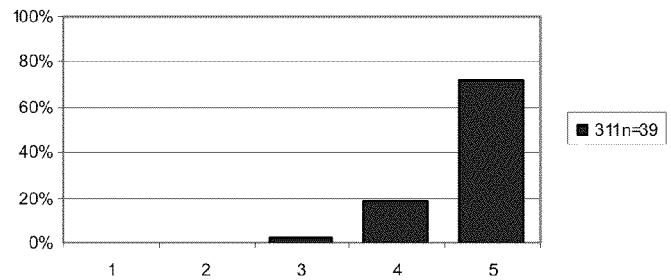
Figure 5:
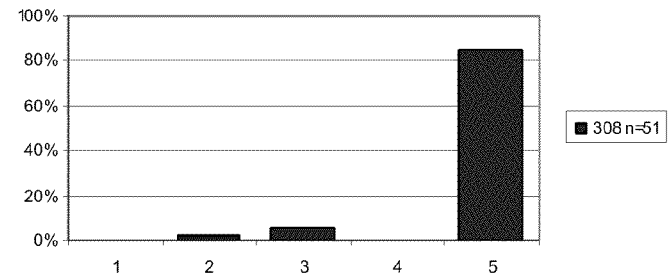
Figure 5:
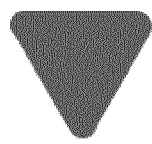
Figure 5:
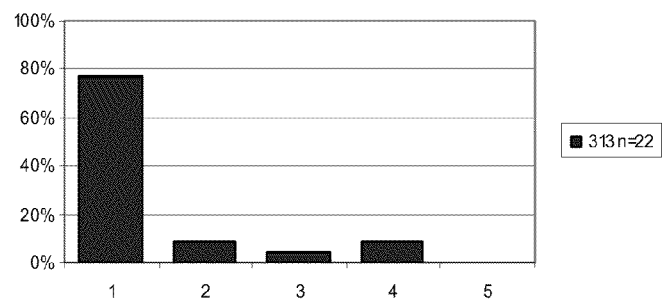
Figure 5:
Figure 5:
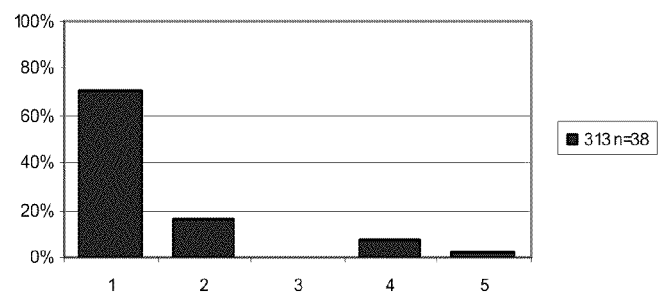
Figure 5:
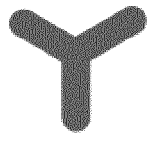
Figure 5:
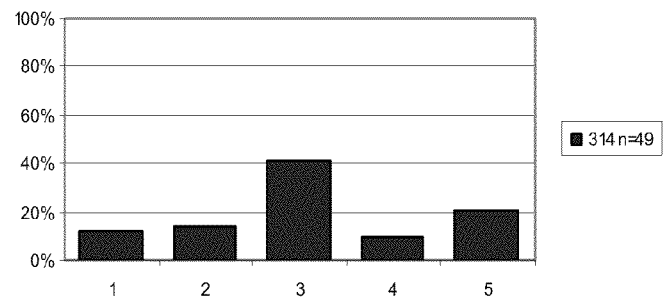
Figure 5:
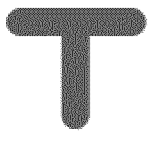
Figure 5:
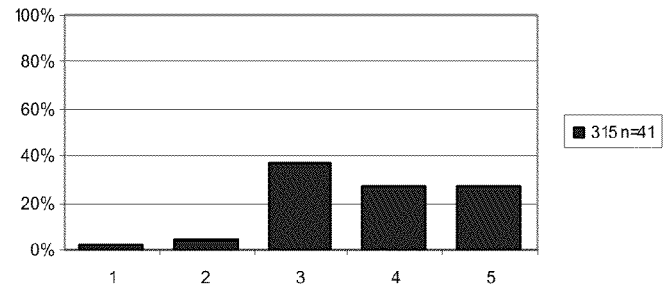
Figure 5:
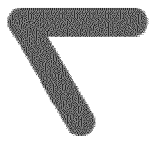
Figure 5:
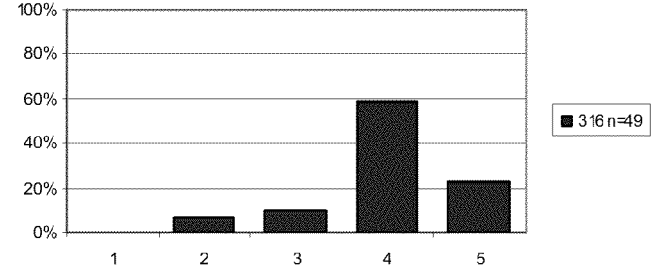
Figure 5:
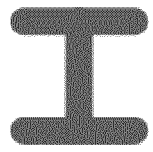
Figure 5:
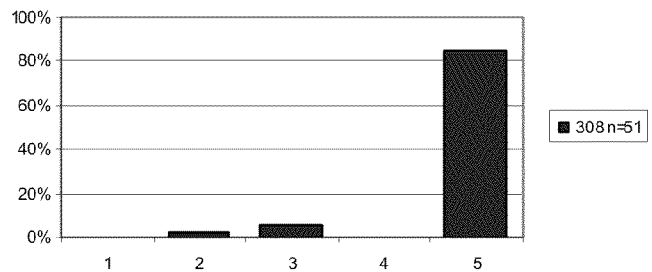
Figure 5:
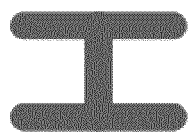
Figure 5:
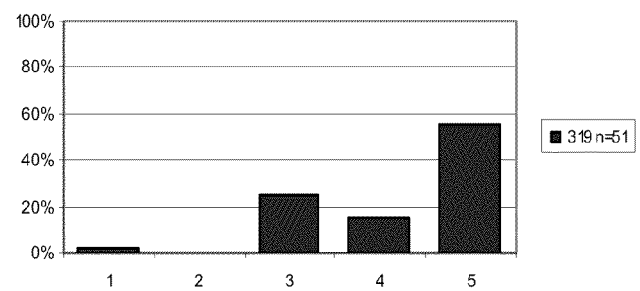
Figure 5:
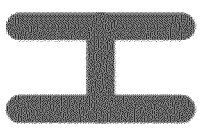
Figure 5:
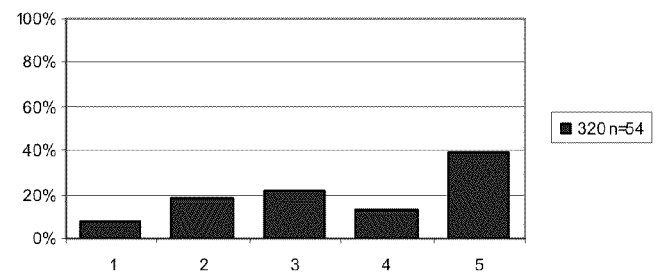
Figure 5:
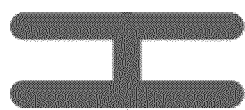
Figure 5:
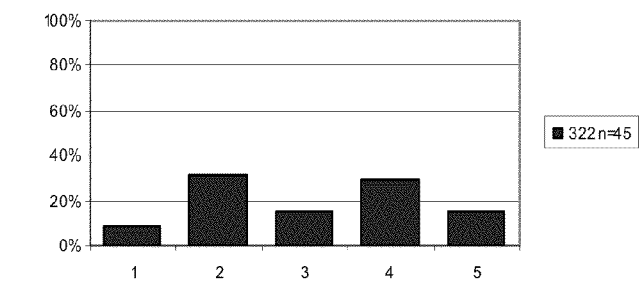
Figure 5:
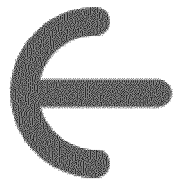
Figure 5:
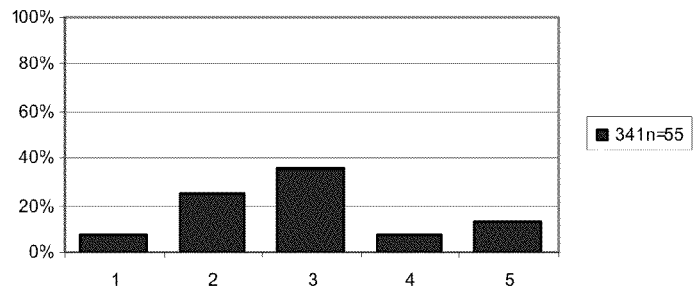
Figure 5:
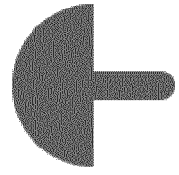
Figure 5:
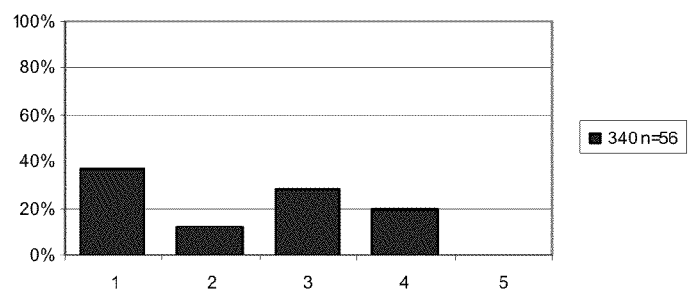
Figure 5:
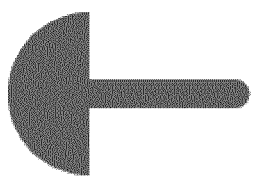
Figure 5:
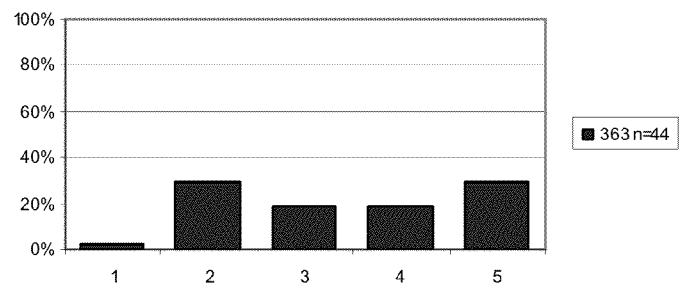
Figure 5:
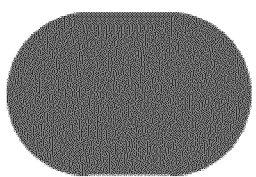
Figure 5:
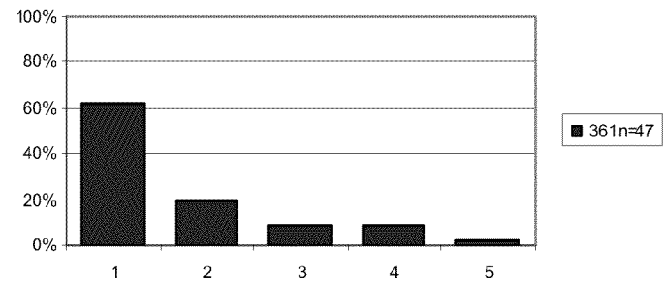
Figure 5:
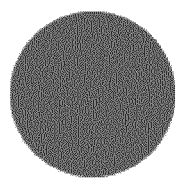
Figure 5:
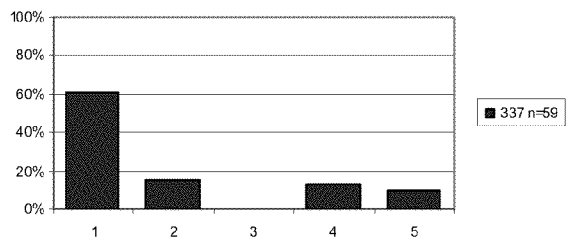
Figure 5:
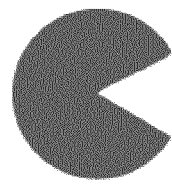
Figure 5:
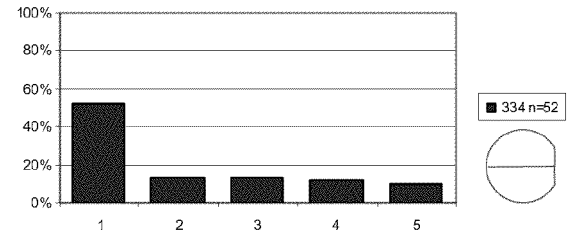
Figure 5:
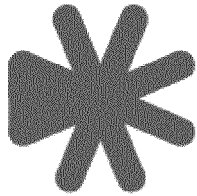
Figure 5:
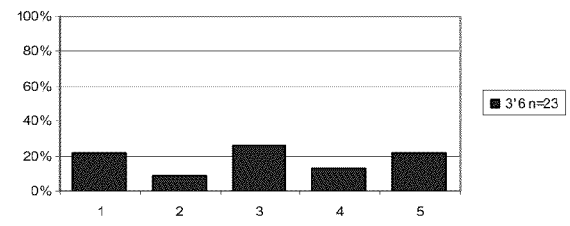
Figure 5:
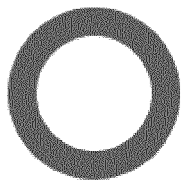
Figure 5:
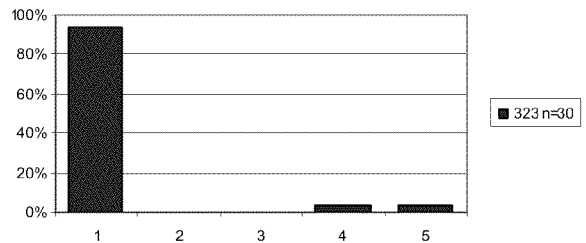
Figure 5:
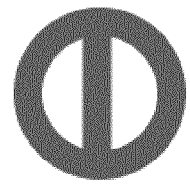
Figure 5:
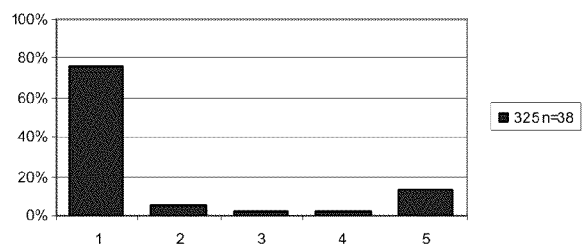
Figure 5:
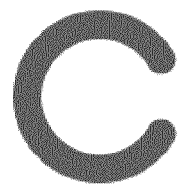
Figure 5:
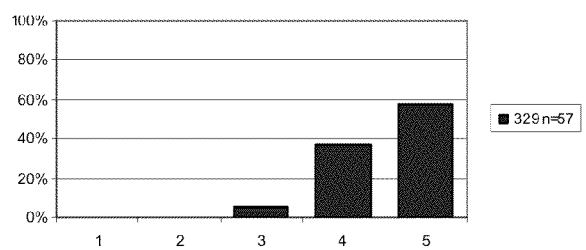

FIG. 5: Five different schematic behaviours of cells on a support. (1) cells move around each others in one direction, more precisely move persistently around each others in one direction or the other (clockwise or counter clockwise); (2) cells move around each other in the two directions (in other words, cell move without any stop but can change their direction); (3) cells move around each other, stop and start again to move around each other; (4) cells oscillate around a same position and are almost at the equilibrium; (5) cells are stable around a unique position. The patterns allowing reaching equilibrium are those where cells are found in the majority in behaviours (4) and (5). The patterns not allowing reaching equilibrium are those where cells are found in the majority in behaviours (1) and (2), preferably found in the majority in behaviours (1), (2) and (3).

The behaviour of two MCF10A epithelial daughter cells was monitored by phase contrast microscopy for different shapes of adhesive patterns.

Figure 6:
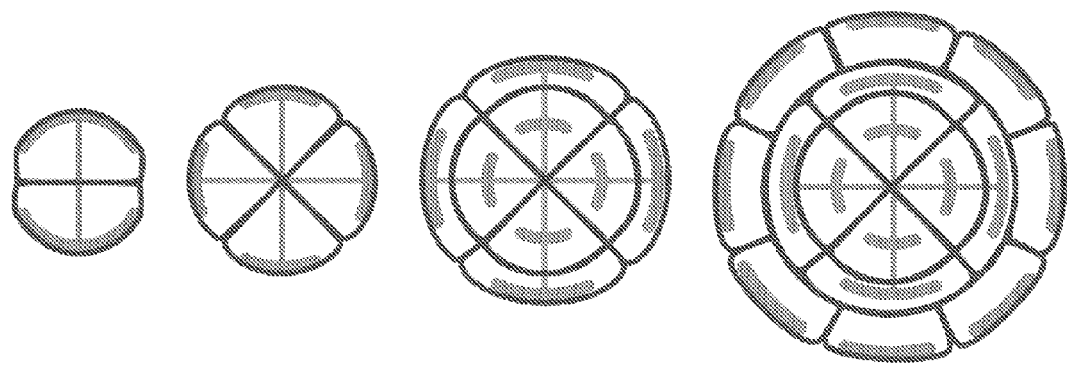

FIG. 6: Example of adhesive pattern for multiple cells arrangement.

Figure 7:
Figure 7:
Figure 7:
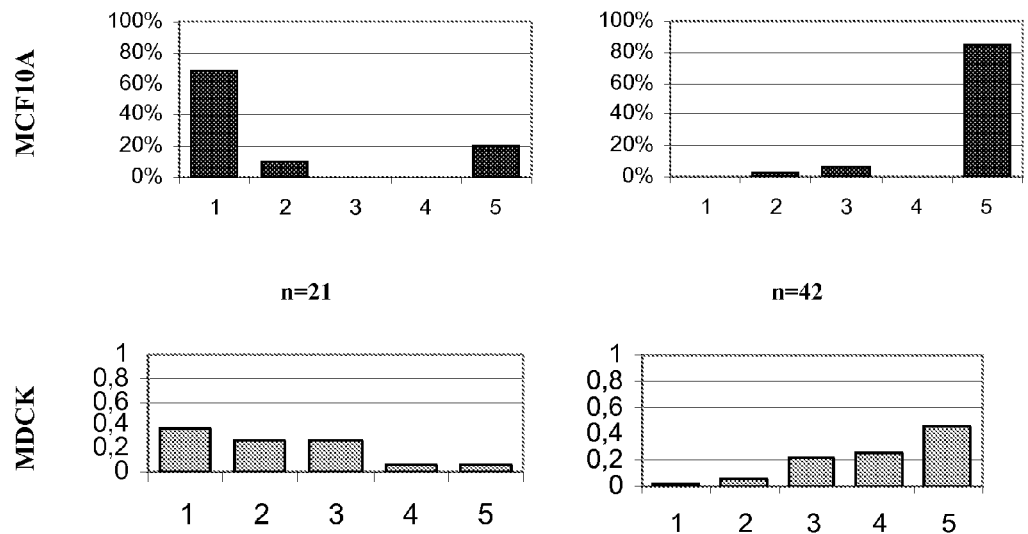

FIG. 7: The behaviour of either two MDCK and MCF10A epithelial daughter cells was monitored by phase contrast microscopy for two different shapes of adhesive patterns. The meaning of the five schematic behaviours of cells on a support is disclosed in the legend of FIG. 5. MCF10A and MDCK cells behaviours on the two patterns follow the same tendency: stabilization on H and destabilization on "frame".

Figure 8:
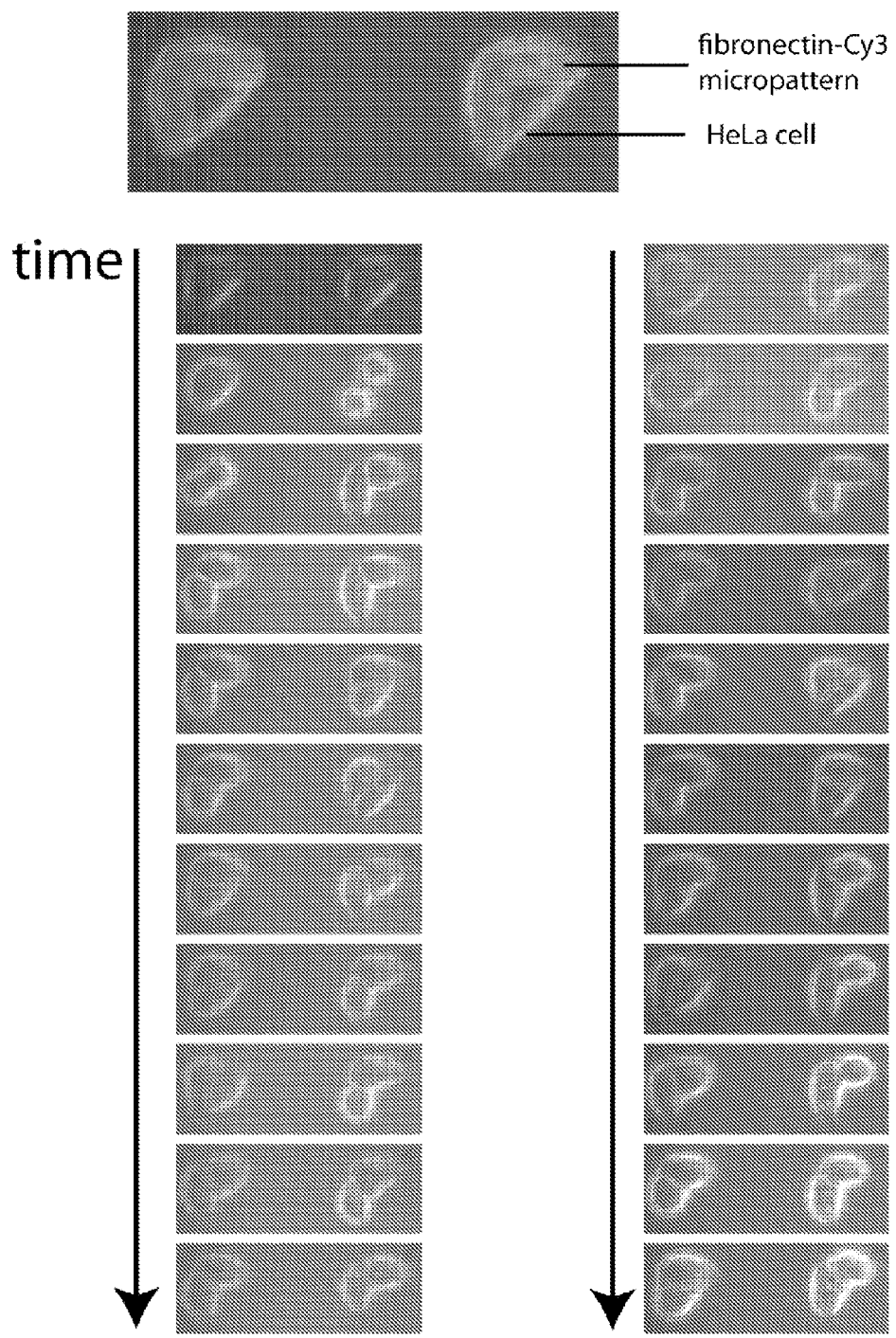

FIG. 8: Images illustrating the behaviour of two daughter Hela cells on a L adhesive pattern as disclosed in WO 2005/026313. Cultured HeLa cells were synchronised in order to be in the G2 phase. Cells were then trypsinized, plated on the micropatterns and video-recorded for 30 hours with a 10 minutes time-frame. Cells rapidly entered mitosis on each pattern. After division the two daughter cells were seen to move around each other without reaching a stable multicellular equilibrium. The 22 images displayed have been chosen and extracted from the entire time-sequence in order to concisely illustrate cell divisions and cell movements after division. Two examples are shown in order to illustrate the reproducibility of these movements and the absence of stable state in cell pair.

DETAILED DESCRIPTION OF THE INVENTION

Definition

By "convex envelop" is intended the minimal convex polygon containing the adhesive pattern. By the "area defined by the convex envelop" is intended the area covered by the zone comprised in the convex envelop. By "S" is intended to refer to the surface covered by a eukaryotic cell on a support without any constraint (e.g., a cell on a Petri dish or a glass coverslip). By "D" is intended to refer to the diameter of the disk having the said surface S.

By the "distance between the two adhesive patterns" is intended the distance between the two closer points of the two adhesive patterns.

By "about" is intended the value more or less than 5%.

By "mechanical equilibrium" or "mechanically stable" is intended that cells oscillate around a same position and are almost at the equilibrium (behaviour 4 as defined in FIG. 5 and in examples) and cells are stable around a unique position (behaviour 5 as defined in FIG. 5 and in examples). In particular, cell behaviour can be recorded every 5 minutes, during one cell division period for instance (e.g., about 24-48 hours). Alternatively, "mechanical equilibrium" or "mechanically stable" can also be defined by a rate of 80% of cells whose axis joining the nuclei of the two considered cells varies less than 45°, preferably of less than 40°, 35°, 30° or 20°, with respect to a fixed reference axis on the micropattern. These measures are preferably performed at the culture temperature for the considered cells, for instance at 37° C. By "reproducible conformation" is intended to refer to the fact that the cells adopt the same conformation in the multicellular arrangement for the considered set of patterns.

The inventors provide the rules allowing the design of a device for adhering at least two cells in a multicellular arrangement with a mechanically stable and reproducible conformation. The design of a device for adhering several cells in a multicellular arrangement with a mechanically stable and reproducible conformation is a new concept. The rules are the followings and have been deduced from experimental data, in particular those shown in FIG. 5: one adhesive pattern for each cell of the multicellular arrangement. The zone between the at least two adhesive patterns has been called intercalating area. The adhesive patterns are sufficiently separated from each other by an essentially non-adhesive intercalating area for preventing a cell on a first adhesive pattern to reach another adhesive pattern. Of course, the adhesive patterns have also to be sufficiently near to allow the interaction between the cells. It has been established that the intercalating area is about one diameter of the cell's surface (D). The adhesives patterns are preferably less than the surface area of the cell (S). These small adhesive patterns are important as they provide the cells with a sufficient freedom degree (by the non-adhesive area) to allow them wedging one against each other. The equilibrium between those two constraints (the adhesive pattern and the other interacting cell) stabilizes the interacting cells and allows them to adopt a natural position, therefore stable and reproducible. In order to provide sufficient freedom degree to the cells, the intercalating area is essentially non-adhesive. However, the intercalating area may include adhesive area, more preferably a single adhesive area, thereby helping the cells to meet each other and establish the interaction contact. The width of this adhesive area of the intercalating zone has to be narrow (less than ½ cell's diameter). Indeed, if this area is too large, it can allow the cell reaching the other adhesive pattern. The area of the two adhesive patterns with the intercalating area is sufficient to adhere two animal cells. Of course, in order to avoid the disturbance of the multicellular arrangement by surrounding cells (not involved in the multicellular arrangement), each set of patterns is surrounded by a cytophobic region.

The device of the present invention comprises a plate defining a surface, and a set of at least two adhesive patterns being sufficiently separated from each other by an essentially non-adhesive intercalating area for preventing a cell on a first adhesive pattern to reach another adhesive pattern and the area of the at least two adhesive patterns with the intercalating area is sufficient to adhere two animal cells. In other words, the area covered by the at least two adhesive patterns and the intercalating area is sufficient to adhere two animal cells and each cell adheres to one individual adhesive pattern. In particular, the plate defines a plane surface. In particular, the area covered by the at least two adhesive patterns and the intercalating area is too large for being covered by a single cell. Accordingly, this area is far more than 1 S, and for a multicellular arrangement of x cells, this area is about x S. For instance, for a multicellular arrangement of 2 cells, this area will be about 2 S.

The area defined by the convex envelop of each adhesive pattern is comprised between about ½ S and about ³⁄₂ S, S being the area covered by a cell without any constraint. In a preferred embodiment, the area defined by the convex envelop of each adhesive pattern is comprised between about ¾ S and about ⁵⁄₄ S, more preferably about S. For instance, S can be comprised between 1 and 2,500 µm², more preferably between 1 and 1,000 µm², still more preferably between 1 and 500 µm² or 500 to 900 µm². S may depend on the cell type. However, the area defined by the convex envelop of each adhesive pattern includes a high percentage of non-adhesive area, for instance at least 20, 30, 40 or 50%, preferably between 20-70%, 30-60%, or 40-50% of non-adhesive area. Alternatively, the area covered by the adhesive pattern for each cell is less than 80, 70, 60 or 50% of the cell surface S. For instance, the area of each adhesive pattern is between 30-80%, 40-70% or 50-60% of the cell surface S. This area could also be defined as the surface covered by one cell once the mechanical equilibrium is reached.

The convex envelop of each adhesive pattern can have any kind of form (e.g., disk, square, rectangle, trapezoid, disk fragment, ellipse, etc. . . . ). On this convex envelop, it can be defined a long axis and a short axis.

The adhesive pattern can be formed of single connected adhesive surfaces and/or of several non-connected adhesive surfaces. By "single connected adhesive surface" is preferably intended a solid line or curve. By "non-connected adhesive surfaces" is preferably intended dotted or dashed line or curve, or discrete point or area. In a preferred embodiment, the adhesive pattern consists of a combination of adhesive elements selected from a line, a curve and a point. The width of the adhesive point, lines, curves or edges is preferably between 0.1 to 100 µm, more preferably between 1 to 50 µm, still more preferably about 8 µm.

In a preferred embodiment, the distance between two adhesive patterns is comprised between about ⅔ D and about ⁴⁄₃ D. In a preferred embodiment, the two adhesive patterns are separated by a distance of between about ¾ D to about ⁵⁄₄ D, more preferably about D.

In a preferred embodiment, the essentially non-adhesive intercalating area comprises a single adhesive zone. The single adhesive zone is suitable for not allowing a cell to reach another adhesive pattern. That is to say that this single adhesive zone has to be narrow. Indeed, a long and fine adhesive line parallel to the large axis of the adhesive pattern is not appropriate because it can allow the cell to reach another adhesive pattern. For instance, the adhesive zone is a zone located between two adhesive patterns and having a width of less than D, preferably less than ½ D, preferably less than ⅓ D, more preferably less than ¼ D. In one embodiment, the adhesive zone can connect two adhesive patterns, for instance as a line or a curve. In another embodiment, the adhesive zone can be between the two adhesive patterns without any connection with them. While not wishing to be bound by theory, it is thought that this adhesive zone helps the two cells to establish the cell-cell interaction. In a preferred embodiment, 50% of the essentially non-adhesive intercalating area is non adhesive, more preferably 60, 75, 80, 85 or 90%. The single adhesive zone can be comprised of a single connected adhesive surface and/or of several non-connected adhesive surfaces forming the adhesive zone.

In a most preferred embodiment, the device of the invention is such that the distance between two adhesive patterns is comprised between about ⅔ D and about ⁴⁄₃ D, preferably between about ¾ D to about ⁵⁄₄ D, more preferably about D; the essentially non-adhesive intercalating area comprises a single adhesive zone, said single adhesive zone being located between two adhesive patterns and having a width of less than D, preferably less than ½ D, preferably less than ⅓ D, more preferably less than ¼ D; and, the area covered by the adhesive pattern for each cell is less than 80, 70, 60 or 50% of the cell surface S.

In a particular embodiment, a set of two adhesive patterns can adopt the following forms: C, X, H, Z and Π. Indeed, the present experiments (FIG. 5) demonstrate that these forms are well-appropriate to reach a mechanical equilibrium.

The present invention also contemplates a device with more than two adhesive patterns. The rules established for an arrangement of two cells also apply for a multicellular arrangement with more than two cells. In this case, the outline of the set of patterns is made of the alternation of adhesive and non-adhesive areas so that the cells are positioning on the adhesive areas and establishing contacts with the neighbouring cells on the non-adhesive areas. Each adhesive pattern is separated from the others by an essentially non-adhesive area. The distance between two adhesive patterns is comprised between about ⅔ D and about ⅘ D. In a preferred embodiment, the two adhesive patterns are separated by a distance of between about ¾ D to about 5/4 D, more preferably about D. However, the essentially non-adhesive intercalating area comprises a single adhesive zone. For instance, the adhesive zone is a zone located between two adhesive patterns and having a width of less than D, preferably less than ½ D, preferably less than ⅓ D, more preferably less than ¼ D. In one embodiment, the adhesive zone can connect two adhesive patterns, for instance as a line or a curve. In particular, the device can have a set of 4, 8, 16 or 32 adhesive patterns with the same rules: a distance between each adhesive pattern and an optional narrow single adhesive zone between each pair of adhesive patterns. FIG. 6 schematically illustrates a set of 4, 8, 16 or 32 adhesive patterns. Such set of adhesive patterns designed for a multicellular arrangement with more than two cells covers an area of more than 2500 $\mu m^2$, preferably between 2600 and 50000 $\mu m^2$, for instance 2600, 3000, 3500, 4000, 4500, 5000, 6000, 7000, 8000, 9000, 10000, 20000, 30000, 40000 or 50000 $\mu m^2$.

Preferably, said device comprises a plurality of sets of at least two adhesive patterns isolated from each other's by cytophobic regions to which cells do not adhere. More particularly, said device comprises at least 2 sets of at least two adhesive patterns, preferably at least 5, 10, 100, 1000, 10000, or 100000 sets of at least two adhesive patterns. In a preferred embodiment, said device comprises between 5 and 25000 sets of at least two adhesive patterns/$cm^2$, more preferably between 5000 and 10000 sets of at least two adhesive patterns/$cm^2$, still more preferably about 7500 sets of at least two adhesive patterns/$cm^2$.

The adhesive pattern or zone comprises molecules that promote cell attachment. These molecules can be non specific like oxidized polystyrene like in tissue culture treated polystyrene dish. The molecules can also be specific adhesion molecules such as the one that are well known to those of ordinary skilled in the art and comprise antigens, antibodies, cell adhesion molecules, extracellular matrix molecules such as laminin, fibronectin, synthetic peptides, carbohydrates and the like. Preferably, said adhesive patterns comprise extracellular matrix molecules, more preferably fibronectin.

The non adhesive surface is an inert surface. An appropriate inert surface is a surface covered by a derivative of poly (ethylene glycol).

The plate is a support convenient for confocal, optical and/or fluorescence microscopies. In the more preferred embodiment, the plate is glass, possibly covered with a thin layer of oxydized polystyrene. For example, a convenient plate according to the present invention is a coverslip or a slide. It can also be a tissue culture treated Petri dish. It is understood in the present invention that the plate refers to a plane surface without any well.

The device according to the present invention can comprise several groups of a set of adhesive patterns on the same plate separated from each other such that each group can be incubated in a different medium. For instance, a group of a set of adhesive patterns can be contacted with a test compound and another group can be contacted with another test compound or without any test compound. This separation can be provided by a physical barrier such as teflon seal. For example, see SPI Teflon® of SPI Supplies, Teflon® Printed Slides of Aname.

The device according to the present invention with adhesive patterns and zones, and the cytophobic regions are formed by micropatterning. Microcontact printing or UV patterning can be used. Standard methods are well known by those skilled in the art. For review, see Whitesides et al (Annu Rev. Biomed. Eng., 2001, p. 335-373, more particularly p. 341-345). In particular, the device can be prepared by a method comprising:
  preparing a master template with at least one adhesive pattern;
  preparing a stamp from said master template;
  inking said stamp with molecules that promote cell attachment;
  contacting the inked stamp with the plate;
  making cytophobic the non-printed surface of the plate.

Preferably, the master template is prepared from a silicon wafer coated with a photoresist layer by illuminated with UV through a mask on which the adhesive pattern has been designed. The stamp is preferably poly(dimethylsiloxane) (PDMS) or another siloxane-based polymer. Preferably, said non printed surface of the plate are made cytophobic by an incubation with an inert material such as derivatives of polyethyleneglycol.

A particular example of the preparation of a plate according to the present invention is detailed the example section.

The micropatterning allows a precise control of cells' position at micron scale. The use of glass coverslips without any gold or other metal coating is compatible with every optical imaging technique and especially with epifluorescence on an inverted microscope for video-microscopy. The automation of many 4D acquisitions (3D in time-lapse) is very easy: with a motorized XY stage, one only needs to record the XY position of the first cell as all the others can be deduced from the first one by a known iterative translation; a 100× objective on a ceramic piezoelectric device makes the 3D stack acquisition very fast. Glass coverslips and micropatterning allow one to perform high throughput 3D cell screening at high magnification using epifluorescence as well as transmitted light. When cells are synchronized before seeding, one can get at the description of a "mean cell" by summing the observation of as many cells as necessary. It provides a very accurate description of cells' organization or behaviour as cells are very similar if not identical. From such a "mean cell" description, one can place adequate thresholds for screening active drugs on a particular cell function or genes whose inactivation impairs that function.

The device according to the present invention can be useful in a wide array of cellular biology applications, both in fundamental and applied research field, including cell culturing, tissue engineering, cytometry, toxicology, drug screening, immobilization of cells, cell therapy and biopsy's cell diagnostic. In particular, the devices of the invention are useful as a device to control or constrain cell groups in a reproducible arrangement or configuration. They are also useful for organizing or controlling cell positions in a tissue-like cell culture device. Indeed, the devices allow the control of the individual cell position within cell groups or multicellular arrangements in culture. They permit to get reproducible cell positioning and organization within multicellular island in culture, in particular full control on cell-extracellular matrix and cell-cell adhesion spatial positioning within multicellular arrangements/cell groups. The devices of the invention have an interest in the applied research field because they allow the normalization of cell positioning with cell groups in culture in a reproducible fashion. More particularly, controlled and oriented cell polarities within multicellular structures may be obtained with such a device. Accordingly, the device of the invention can be used to obtained large array of reproducible multicellular groups with control positioning of cell-cell junctions. At the difference of 3D multicellular arrangements, the device is appropriate for regular and reproducible cell positioning within planar multicellular looking like "planar embryoid bodies".

The invention relates to a method for adhering at least two interacting cells in a multicellular arrangement with a mechanically stable and reproducible conformation, comprising:
- selecting the cells to be adhered;
- selecting an appropriate device of the invention; and,
- culturing the cells on the selected device.

The method may comprise determining the surface covered by the cells on a support without any constraint in order to determine the size of the cells and selecting the device based on the cell size. For a multiarrangement of x cells, the appropriate device is selected in order that the area of the x adhesive patterns with the intercalating area is sufficient to adhere the x cells.

Therefore, the invention concerns a method for culturing at least two cells on a surface or in a medium on a surface, said method comprising:
- providing a plate defining a surface and at least two adhesive patterns according to the present invention, preferably a device according to the present invention; and,
- culturing the cells on said set of adhesive pattern(s) or in a medium on said adhesive pattern(s).

The medium can be any medium convenient for the cell culture. For instance, the medium can be Dulbecco Modified Eagle Medium with 10% calf serum, 50 µg/mL penicillin and streptomycin and 2 mM glutamine.

The invention also concerns a method for immobilizing at least two interacting cells in a mechanical equilibrium at a surface, said method comprising:
- providing a plate defining a surface and at least two adhesive patterns according to the present invention, preferably a device according to the present invention; and,
- exposing the plate to at least one cell for a period of time sufficient to allow the cell(s) to divide into at least two cells on said set of adhesive patterns and to adhere to each said adhesive pattern and reach a mechanical equilibrium.

Alternatively, the invention also concerns a method for immobilizing at least two interacting cells in a mechanical equilibrium at a surface, said method comprising:
- providing a plate defining a surface and at least two adhesive patterns according to the present invention, preferably a device according to the present invention; and,
- exposing the plate to at least two cells for a period of time sufficient to allow the cell(s) to adhere to each said adhesive pattern and to reach a mechanical equilibrium.

The invention further concerns a method for studying the shape, the cell movement and migration, the cell-cell interaction, the cell architecture, the cell differentiation, the cell polarity, the global internal cell organization, the cell division and/or any function of cells, said method comprising:
- providing a plate defining a surface and at least two adhesive patterns according to the present invention, preferably a device according to the present invention;
- exposing the plate to at least one cell for a period of time sufficient to allow the cell(s) to divide into at least two cells on said set of adhesive patterns and to adhere to each said adhesive pattern and reach a mechanical equilibrium; or exposing the plate to at least two cells for a period of time sufficient to allow the cell(s) to adhere to each said adhesive pattern and to reach a mechanical equilibrium;
- growing the cells on the adhesive patterns; and,
- observing the cell shape, the cell movement and migration, the cell-cell interaction, the cell architecture, the cell differentiation, the cell polarity, the global internal cell organization, the cell division and/or any function of cell(s).

In a particular embodiment, the global cell organization and cell polarity are evaluated through, but not limited to, the observation of the centrosome and the primary cilium positions, the nucleus position, the Golgi apparatus structure (i.e. CGN and TGN), the localization of cell adhesion (such as cadherins and integrins), the network of actin (e.g., the spatial distribution of actin filaments), and/or tubulin, and/or intermediate filaments, the routes of the internal transport of molecule.

In another embodiment, cell migration is quantified by following nuclei movements and cell-cell contact plane displacement.

In another embodiment, the cell-cell interaction is quantified by analysing the protein composition (such as cadherin or beta-catenin) and the position of the cell-cell contact with immuno-histochemistry.

In another embodiment, the cell architecture is described by measuring the size and positions of cytoskeletal elements such as actin fibres, microtubules and intermediate filaments.

In another embodiment, the cell differentiation is assessed by detecting the presence of specific determinants such as transcription factors in the cells nuclei, or messenger RNA or micro RNA or specific receptors in the cell cytoplasm or at the cell surface that can influence cell differentiation.

In another embodiment, the cell division is analysed by quantifying the number of mitotic spindle pole, the movement of spindle poles during spindle formation, the size of the mitotic spindle, the orientation of spindle poles with respect to cell-cell and cell-extracellular matrix adhesions, the localisation of specific proteins in the cell membrane that influence spindle poles positioning, the final position of daughter cells with respect to the micropattern or the respective size and possibly unequal protein content of daughter cells.

In another embodiment, the method comprises an automated analysis of said cell(s) using an image analyser including a specific software using an algorithm designed for such analysis. More particularly, the specific software allows performing the automated method described above.

Any kind of animal cell can be used in the present invention. Cells can be from animal, mammalian, or human. Cells can be for example fibroblast, endothelial and epithelial cell. In a preferred embodiment, the cells are epithelial cells. Cells can be derived from a healthy or pathologic tissue or organism. The cells can be wild-type or modified cells. In a particular example, the cells can be a tumor cell. For example, a gene can be inactivated and these methods allow the identification of the genes which are involved in the cell shape, cytoskeletal architecture, cell migration, cell adhesion, in internal cell transport of molecules, in the global internal organization, in the compartmentation, in the spindle formation or orientation, in the differentiation, etc. . . .

The invention concerns the use of a device according to the present invention for screening compounds of interest which modifies the cell shape, the cell movement and migration, the cell architecture, the global internal organization of the cells, the cell polarity, the mitosis or cell division, the cell differentiation, the cell-cell interactions or any function of the cell. The invention also concerns the use of a device according to the present invention to identify genes of interest which are involved the cell shape, cytoskeletal architecture, cell migration, cell adhesion, the global internal organization of the cells, the mitosis, the cell differentiation, the cell-cell interactions or any function of the cell.

The invention further concerns a method for screening compounds of interest using the device according to the present invention. Indeed, this device allows high-throughput screening since the cells have a stationary and reproducible conformation, a mechanical equilibrium with optionally a controlled global internal organization of the cells. This device allows the observation of the effect of the test compounds on the cell shape, the cell movement and migration, the cell-cell interaction, the cell architecture, the cell differentiation, the cell polarity, the global internal cell organization, the cell division and/or any function of cell(s). More particularly, the invention concerns a method of selecting biologically active compounds, said method comprising:

providing a device according to the present invention;
    exposing the plate to at least one cell for a period of time sufficient to allow the cell(s) to divide into at least two cells on said set of adhesive patterns and to adhere to each said adhesive pattern and reach a mechanical equilibrium; or exposing the plate to at least two cells for a period of time sufficient to allow the cell(s) to adhere to each said adhesive pattern and to reach a mechanical equilibrium;
    contacting a test compound with said cells;
    growing the cells on the adhesive patterns; and,
    observing the cell shape, the cell movement and migration, the cell-cell interaction, the cell architecture, the cell differentiation, the cell polarity, the global internal cell organization, the cell division and/or any function of cell(s)

In an alternative embodiment of the screening method, the cells can be grown on the adhesive patterns before to be contacted with the test compound. Thus, it can be possible to evaluate the effect of the compound on the existing shape, the existing cell-cell contact and the organization of the cell.

In another alternative embodiment, the cells are contacting with the test compound before to be adhered to the plate. Accordingly, the method comprises:

providing a device according to the present invention;
    contacting a test compound with cells;
    exposing the plate to at least one of said cells for a period of time sufficient to allow the cell(s) to divide into at least two cells on said set of adhesive patterns and to adhere to each said adhesive pattern and reach a mechanical equilibrium; or exposing the plate to at least two of said cells for a period of time sufficient to allow the cell(s) to adhere to each said adhesive pattern and to reach a mechanical equilibrium;
    growing the cells on the adhesive patterns; and,
    observing the shape, the cell movement and migration, the cell-cell interaction, the cell architecture, the global internal cell organization, the cell differentiation, the cell polarity, the cell division and/or any function of said cells.

Preferably, the method comprises an additional step of comparing the cell shape, the cell movement and migration, the cell-cell interaction, the cell architecture, the cell differentiation, the cell polarity, the global internal cell organization, the cell division and/or any function of cell(s) with cells not contacted by said test compound. Optionally, said control cells can be contacted with a reference compound with known effect.

The test compound may be of various origin, nature and composition. It may be any organic or inorganic substance, such as a lipid, peptide, polypeptide, nucleic acid, small molecule, etc., in isolated or in mixture with other substances. For instance, the test compound can be an antibody, an antisense oligonucleotide, or an RNAi. The compounds may be all or part of a combinatorial library of products, for instance.

Of course, in the above-mentioned methods, the cells are in a multicellular arrangement, in particular with a mechanical equilibrium. Indeed, the goal of the device according to the invention is to be able to study or screen cells in the context of interacting cells and the mechanical equilibrium and reproducibility are required in order to be suitable for high throughput data acquisition and high sampling.

Further aspects and advantages of the present invention will be disclosed in the following experimental section, which should be regarded as illustrative and not limiting the scope of the present application.

EXAMPLES

Several patterning method can be used to fabricate the micropatterns described in the invention. Two main methods, the microcontact printing or the UV patterning are adapted. The microcontact printing relies on the deposition of adhesion molecules with a stamp and the backfilling with a cytophobic component. The UV patterning method relies on the coating of the substrate with a cytophobic component which is further oxydized with UV light in specific patterns with a laser or an optical mask. Here, is described in details the microcontact printing method.

Microcontact printing method

The method used is based on the use of an elastomeric stamp with micro-features to print the proteins on the substrate of choice. The entire process can be subdivided into three main parts. The first part describes the fabrication of a silicon master that will be used to make the stamp. The second part describes the fabrication and use of the poly-dimethylsiloxane (PDMS) stamp. The stamp is inked with extracellular matrix proteins and dried. Proteins are then printed on either a tissue culture polystyrene dish or a glass slide covered with a thin layer of polystyrene (PS). The non printed areas are back-filled with poly-L-Lysine-poly-ethyleneglycol (PLL-PEG).

I Master Fabrication

Materials
    Reagents
    Acetone
    Developer LDD26W (Shipley, Coventry, UK)
    Chlorotrimethylsilane (Sigma-Aldrich, Saint Quentin Fallavier, France)
    Optical mask (Deltamask, Netherlands)
    Photoresist SPR220-7.0 (Shipley)
    Silicon Wafer 100 mm (MEMC Spa, Italia, ref GPHVXB6F)

Method

Photoresist Layer Coating
    1—Silicon wafer was cleaned by 10 minutes sonication in acetone and dried with filtered air flow or nitrogen flow.
    2—The silicon wafer was placed on a spin coater. ⅔ of the surface was covered with the photoresist. Then the photoresist was spin-coated at 2000 rotations-per-minute during 1 minute.
    3—The wafer and the photoresist layer were baked on a hot plate for 3 minutes at 115° C. The wafer was let on the bench for 15 minutes in order to return to room temperature. These three steps resulted in a 9 micron-thick layer of photoresist on the silicon wafer.

Photoresist Lithography

4—The photoresist layer and the optical mask were place into contact on the mask aligner and illuminated with the UV lamp (UV source 405 nm, UV power 6 mW/cm$^2$) for 45 seconds.

5—The photoresist was developed 2 minutes in pure developer and transferred in a distilled water bath to be rinsed and to stop revelation. The illuminated areas got dissolved in the developer (because the chosen photoresist is positive, negative resists would give the opposite result). This created the micro-features. The obtained resist master mould was then dried with filtered air flow.

Photoresist Master Surface Coating

6—To prevent a strong adhesion of PDMS during stamp fabrication the resist master was silanized. The resist master was placed into a vacuum dessicator close to a small beaker containing few drops of chlorotrimethylsilane. The vacuum was made for 30 minutes to help the formation of chlorotrimethylsilane vapours. Then the dessicator was shut and the resist master was let in the presence of the vapour overnight.

7—The resist master was placed in the oven at 100° C. for 30 minutes to complete silane organization on the master surface.

II Micropatterned Substrate Fabrication

Two substrates for micropatterning were presented: the glass slide, which ensures the best optical quality, and the tissue culture treated poly-styrene (TCPS) dish. Since protein adhesion was much better on oxidized PS than on glass, glass slides had to be coated with a thin PS layer.

Materials

Reagents
poly-dimethylsiloxane (PDMS) (Sylgard 184 kit, 1 kg, Dow Corning)
Fibronectin (F1141, Sigma)
AP6000
Poly-styrene (Acros)
Toluene
Glass slide
TCPS
A homemade resist master (see preceding part) or a custom commercial master (Biotray, Lyon, France).
Water
Falcon tube
PLL-g-PEG (SurfaceSolutions, Switzerland)
parafilm Method Stamp fabrication 1—PDMS and curing agent (both included in the Sylgard kit 184) were mixed in a plastic beaker in a 10/1 ratio. This induced bubbles formation.

2—PDMS mix was degassed under vacuum to remove air bubbles. The duration depended on the vacuum.

3—A 2 mm thick layer of degassed PDMS mix was cast on the resist master and cured 2 hours at 60° C. in the oven.

4—The PDMS layer was gently pealed-off.

5—The region of interest containing the chosen micropattern geometries can be visually located on a simple microscope with transmitted light. About 1 cm$^2$ stamps were manually cut out of it with a scalpel.

Stamps must be stored in a close package to be kept away from dust. They can be kept for months before being used.

Substrate Preparation

The substrate described here was the glass slide that has to be covered with poly-styrene (PS). The TCPS dish can be used as provided.

6—The glass slide was washed with ethanol. Optionally it can be sonicated in ethanol to optimize dust removal. It was dried with filtered air flow or let dry under the hood.

7—The glass slide was placed on the spin-coater. Few drops of adhesion promoter AP6000 were deposed on the glass and spin-coated at 100 rpm for 10 s (to cover the slide) then 1000 rpm for 20 s (to form a thin layer). After the spin-coating the AP6000 layer was dry.

8—Few drops of PS in solution in toluene (2%) were deposed on the glass covered with AP6000 and spin-coated at 100 rpm for 10 s (to cover the slide) then 1000 rpm for 20 s (to form a thin layer). After the spin-coating the AP6000 layer was dry.

Micro-Contact Printing

9—A 20 µL drop of fibronectin at 50 µg/mL in PBS was deposed on the micro-structured surface of the 1 cm$^2$ stamps. The PDMS being hydrophobic it was necessary to force drop spreading with the tip of the pipetman by bringing it toward each corner of the stamp. The surface of the stamp can be gently touched. The inking lasted 30 minutes to allow fibronectin adsorption on the PDMS (this duration might probably be reduced).

1—This step can be performed during protein adsorption at step 9. To use the glass slide with the PS layer as a substrate: place the slide in the plasma cleaner. The pump was turned on to make the vacuum in the chamber. A weak oxygen flow was opened. The oscillating electric field was applied at 30 W for 10 s. To use the TCPS dish as a substrate: a dish didn't require absolutely plasma oxidation and can be printed as it is provided, but the same plasma treatment as described for glass slide greatly improved printing and passivation efficiencies.

11—After step 9 the fibronectin drop was sucked and a large drop of PBS was added on the surface before it dries. This step was repeated twice to remove unadsorbed fibronectin.

12—The PBS drop was sucked and the stamp was let dry a few seconds to one minute under the air flow of the hood. The stamp was ready for printing when the surface looked dry when looking at reflected light on it.

13—Once dry, the stamp was taken with the tweezers and turned upside-down so as to place the micro-structured surface in contact with the substrate (the TCPS dish or the glass with the PS layer). A short and gentle pressure was applied on it with the tweezers to ensure a good contact between the stamp and the substrate. The stamp was let in contact with the substrate for 1 minute.

14—Stamp was removed and immersed into water in a falcon tube.

15—The printed substrate was immersed in PLL-PEG solution 0.1 mg/mL in Hepes 10 mM at pH 7.4 for 30 minutes. To minimize the amount of PLL-PEG, a 100 µL drop can be placed on the substrate and covered with a piece of parafilm.

16—During PLL-Peg grafting the stamp was cleaned. The tube containing the stamp was heated at 60° C. and sonicated in ultrasound bath 15 minutes. Then the stamp was sonicated in pure alcohol for 15 minutes.

17—The clean stamp was let dry under the hood for one hour and stored back in its package.

18—The PLL-PEG grafted substrate was washed twice with PBS for 2 and 10 minutes.

The substrate was ready for cell deposition. It can be stored dried (and if possible under argon) at 4° C. for at least a week.

III Cell Deposition

Materials
  Reagents
  PBS
  Trypsin-EDTA
  DMEM or DMEM-F12
  SVF
  Penicillin
  Streptomycin Method
1—Adherent cells were washed in PBS and detached from their flask with trypsin-EDTA.
2—Complete culture medium (DMEM or DMEM-F12+ 10% SVF+1% penicillin and streptomycin) was added to the flask and collected cells were centrifugated 3 minutes at 1500 rpm.
3—Surnageant was removed and cells were resuspended in culture medium at 50 000 cells/mL.
4—Cell solution was added on the micropatterned substrate (glass slide or TCPS dish). The final density should be about 10 000 cells per cm$^2$. The whole was placed in the incubator.
5—After a given time that varied from one cell line to the other (one hour for HeLa-B and MDCK) it was checked under the microscope that a sufficiently large proportion of cells had attached to the micro-patterns.
6—Non-attached cells were removed with a flow of medium added to one side of the dish and aspirate on the other.
7—Attached cells were put back in the incubator to let them spread fully.
8—One hour later cells can be fixed or video-recorded.

Results

MCF10A cells, breast epithelial cells, were detached from the flask in which they were cultured and platted on an array of micropatterns. Various geometries of micropatterns have been tested. The micropatterned substrate with cells attached on it is placed on an inverted motorized microscope encaged in an incubator to maintain cells at 37° C. Individual cells were chosen and their positions were recorded. Cell behaviours were video-recorded by taking images in phase contrast every 5 minutes. After cell divisions, the behaviors of daughter cells were observed. The aim was to identify the geometries on which cells adopt a stable and reproducible organisation and to measure the orientation of the cell contact plane with respect to the underlying micropattern.

Cells' behavior was very reproducible on defined patterns. On square shaped micropatterns daughter cells permanently moved around each other (FIG. 2). On H shaped micropatterns daughter cells did not migrate and adopt a stable configuration (FIG. 3). In this case, cell-cell contact was established reproducibly at the same position, above the non adhesive area. Cell pairs on H shaped micropatterns were fixed in methanol at −20° C. and labeled with antibodies against e-cadherin to reveal the cell-cell adhesions and two fluorescent dyes against actin filaments and DNA (FIG. 4).

The inventors defined arbitrary classes to distinguish 5 behaviors to further quantify the stability of cell arrangements on micropatterns. (1) cells move around each other in one direction; (2) cells move around each other in the two directions; (3) cells move around each other, stop and start again to move around each other; (4) cells oscillate around a same position and are almost at the equilibrium; (5) cells are stable around a unique position. The patterns allowing reaching equilibrium are those where cells are found in the majority in behaviours (4) and (5). The patterns not allowing reaching equilibrium are those where cells are found in the majority in behaviours (1) and (2). Hundreds of movies were visually analysed and classified according to the 5 classes. Some geometries like circles, discs, squares and triangles appear to promote cell migration and doublets instability. Others like U, C, V, X or H on which the behaviors (4) and (5) were dominant, appeared to stabilize cells doublets and promote a mechanical equilibrium (FIG. 5).

FIG. 6 shows the behaviour of MDCK cells (Madin-Darby Canine Kidney Cells which are kidney epithelial cells).

FIG. 7 illustrates the behaviour of Hela cells on an adhesive pattern with a L form as defined in WO 2005/026313. It can be observed that the two cells turn around each others. Indeed, this document defines an adhesive pattern designed to allow the adhesion of a single cell. Even if the cell is capable of division on this pattern, it is not adapted to reach a multicellular arrangement with a mechanical equilibrium because it is too small.

The invention claimed is:

1. A method for immobilizing at least two cells at a plane surface in a multicellular arrangement with a mechanical equilibrium, said method comprising:
  providing a device for adhering at least two interacting cells in a multicellular arrangement with a mechanically stable and reproducible conformation that comprises:
  a plate defining a plane surface; and
  a set of at least two adhesive patterns on said plane surface, wherein the at least two adhesive patterns are sufficiently separated from each other by an essentially non-adhesive intercalating area for preventing a cell on a first adhesive pattern to reach another adhesive pattern but sufficiently near to allow interaction between the cells, wherein the distance between two adhesive patterns is between about ⅔ D and about ⅘ D, D being the diameter of a surface S and S is the surface covered by a cell without any constraint, the essentially non-adhesive intercalating area comprising a single adhesive zone that is less than ½ D of S and that optionally connects two adhesive patterns and is suitable for not allowing the cell to reach another adhesive pattern and each adhesive pattern has an area which is less than 80% of S; and, the area covered by the at least two adhesive patterns and the intercalating area is sufficient to adhere at least two animal cells, and wherein the set of at least two adhesive patterns is isolated from other sets by a cytophobic surrounding region; and
  exposing at least 1 adhesive pattern to at least one cell for a period of time sufficient to allow the cell(s) to divide into at least two cells on said adhesive pattern, and to interact with and reach a multicellular arrangement with a mechanical equilibrium with a cell or cells on a second adhesive pattern.

2. The method according to claim 1, wherein the area covered by the adhesive pattern for each cell is less than 70, 60 or 50% of S.

3. The method according to claim 1, wherein said single adhesive zone is a zone located between two adhesive patterns and having a width of less than ¼ D.

4. The method according to claim 1, wherein said single adhesive zone is a zone located between two adhesive patterns and having a width of less than ½ D.

5. The method according to claim 4, wherein said single adhesive zone connects the two adhesive patterns.

6. The method according to claim 1, wherein the set of two adhesive patterns has one of the following forms: C, X, H, Z and Π.

7. The method according to claim 1, wherein the adhesive patterns are formed of single connected adhesive surfaces and/or of several non-connected adhesive surfaces.

8. The method according to claim 1, wherein the device comprises at least 2 sets of at least two adhesive patterns.

9. The method according to claim 1, wherein the device comprises at least 2 sets of at least 4, 8, 16 or 32 adhesive patterns.

10. The method according to claim 9, wherein each set of adhesive patterns is designed for a multicellular arrangement with more than two cells and covers an area of more than 2500 µm$^2$.

11. The method according to claim 1, wherein the area covered by the two adhesive patterns and the intercalating area is about 2 S, S being the surface covered by the cell without any constraint.

12. The method according to claim 1, wherein the area covered by the two adhesive patterns and the intercalating area is about 2 S, S being the surface covered by the cell without any constraint.

13. A method for immobilizing at least two cells at a plane surface in a multicellular arrangement with a mechanical equilibrium, said method comprising:
   providing a device for adhering at least two interacting cells in a multicellular arrangement with a mechanically stable and reproducible conformation that comprises:
   a plate defining a plane surface; and
a set of at least two adhesive patterns, wherein the at least two adhesive patterns are sufficiently separated from each other by an essentially non-adhesive intercalating area for preventing a cell on a first adhesive pattern to reach another adhesive pattern but sufficiently near to allow interaction between the cells, wherein the distance between two adhesive patterns is between about ⅔ D and about ⅘ D, D being the diameter of a surface S and S is the surface covered by a cell without any constraint, the essentially non-adhesive intercalating area comprising a single adhesive zone that is less than ½ D of S and that optionally connects two adhesive patterns and is suitable for not allowing the cell to reach another adhesive pattern and wherein each adhesive pattern has an area which is less than 80% of S; and, the area covered by the at least two adhesive patterns and the intercalating area is sufficient to adhere at least two animal cells, and wherein the set of at least two adhesive patterns is isolated from other sets by a cytophobic surrounding region; and
   exposing at least 1 adhesive pattern to at least two cells for a period of time sufficient to allow each cell to adhere to one of said adhesive patterns, to interact with one another and to reach a multicellular arrangement with a mechanical equilibrium, the interaction between cells being located above the essentially non-adhesive intercalating area.

14. The method according to claim 13, wherein said single adhesive zone is a zone located between two adhesive patterns and having a width of less than ½ D.

15. The method according to claim 14, wherein said single adhesive zone connects the two adhesive patterns.

16. The method according to claim 13, wherein the set of two adhesive patterns has one of the following forms: C, X, H, Z and Π.

17. The method according to claim 13, wherein said single adhesive zone is a zone located between two adhesive patterns and having a width of less than ¼ D.

* * * * *

UNITED STATES PATENT AND TRADEMARK OFFICE
CERTIFICATE OF CORRECTION

| | | |
|---|---|---|
| PATENT NO. | : 8,765,472 B2 | Page 1 of 2 |
| APPLICATION NO. | : 13/121986 | |
| DATED | : July 1, 2014 | |
| INVENTOR(S) | : Thery | |

It is certified that error appears in the above-identified patent and that said Letters Patent is hereby corrected as shown below:

In the Specification

Column 1,
Lines 12-15, "filed October 28, 2008, the disclosures of which are hereby incorporated by reference in their entireties, including all figures, tables and amino acid or nucleic acid sequences." should read --filed October 23, 2008.--.

Column 3,
Line 50, "and II." should read --and Π.--.

Column 5,
Line 59, "each others" should read --each other--.
Line 60, "each others" should read --each other--.
Line 63, "cell move" should read --cells move--.

Column 6,
Line 19, "Hela cells" should read --HeLa cells--.

Column 8,
Line 60, "and II." should read --and Π.--.

Column 9,
Line 42, "ordinary skilled" should read --ordinary skill--.

Column 10,
Line 17, "by illuminated with" should read --by illumination with--.

Column 13,
Lines 34-35, "of cell(s)" should read --of cell(s).--.

Signed and Sealed this
Thirty-first Day of March, 2015

Michelle K. Lee
*Director of the United States Patent and Trademark Office*

CERTIFICATE OF CORRECTION (continued)
U.S. Pat. No. 8,765,472 B2

Column 14,
Line 23, "Several patterning method can" should read --Several patterning methods can--.

Column 15,
Line 4, "were place" should read --were placed--.

Column 16,
Line 26, "1—This" should read --10—This--.

Column 18,
Line 10, "Hela cells" should read --HeLa cells--.